United States Patent [19]

Spector

[11] Patent Number: 5,456,677
[45] Date of Patent: Oct. 10, 1995

[54] METHOD FOR ORAL SPRAY ADMINISTRATION OF CAFFEINE

[76] Inventor: John E. Spector, 2404 Sacada Cir., La Costa, Calif. 92009

[21] Appl. No.: 293,838

[22] Filed: Aug. 22, 1994

[51] Int. Cl.$^6$ .................................................. A61M 35/00
[52] U.S. Cl. ................... 604/290; 604/310; 128/200.14; 128/200.23
[58] Field of Search ................................. 604/290, 310, 604/311; 128/200.14, 200.23; 424/25.43, 58

[56] References Cited

U.S. PATENT DOCUMENTS

| | | |
|---|---|---|
| 3,433,872 | 3/1969 | De Ritter . |
| 4,778,810 | 10/1988 | Wenig et al. . |
| 4,935,225 | 6/1990 | Curtis et al. . |
| 4,953,572 | 9/1990 | Rose et al. . |
| 4,963,367 | 10/1990 | Ecanow . |
| 5,078,129 | 1/1992 | Kleinberg et al. . |
| 5,161,524 | 11/1992 | Evans . |
| 5,219,858 | 6/1993 | Parnell . |
| 5,284,132 | 2/1994 | Geier . |

FOREIGN PATENT DOCUMENTS 8804929  7/1988  WIPO .

OTHER PUBLICATIONS

Handbook of Nonprescription Drugs, (8th Edn, 1986), pp. 364–367.
Drug & Facts and Comparisons, (1994), pp. 1116–1118.

*Primary Examiner*—Randall L. Green
*Assistant Examiner*—Mark O. Polutta
*Attorney, Agent, or Firm*—Brown, Martin Haller & McClain

[57] ABSTRACT

A method and apparatus are disclosed for easily and conveniently self-administering caffeine in combination with a breath freshener. Caffeine, which has important physiological effects as a central nervous system stimulant, is readily, conveniently and effectively administered to humans in a manner neither heretofore recognized nor disclosed, and which uniquely provides for very rapid onset of the stimulatory physiological effect to the user. The caffeine, with a carrier and in combination with a breath freshener, is dispensed as a liquid spray or stream directly onto a person's tongue, from which it is rapidly absorbed in the human system by swallowing and absorption from the intestinal tract or by absorption through the buccal membranes. The caffeine is administered on an as-needed basis in daily quantities of preferably up to 200 mg per four hour period, through one or preferably several metered dosages. The invention is a unique administration method and device, which permits simple and convenient administration of caffeine in a unobtrusive and effective manner on an as-needed basis, with rapid and strong stimulatory effect.

10 Claims, 1 Drawing Sheet

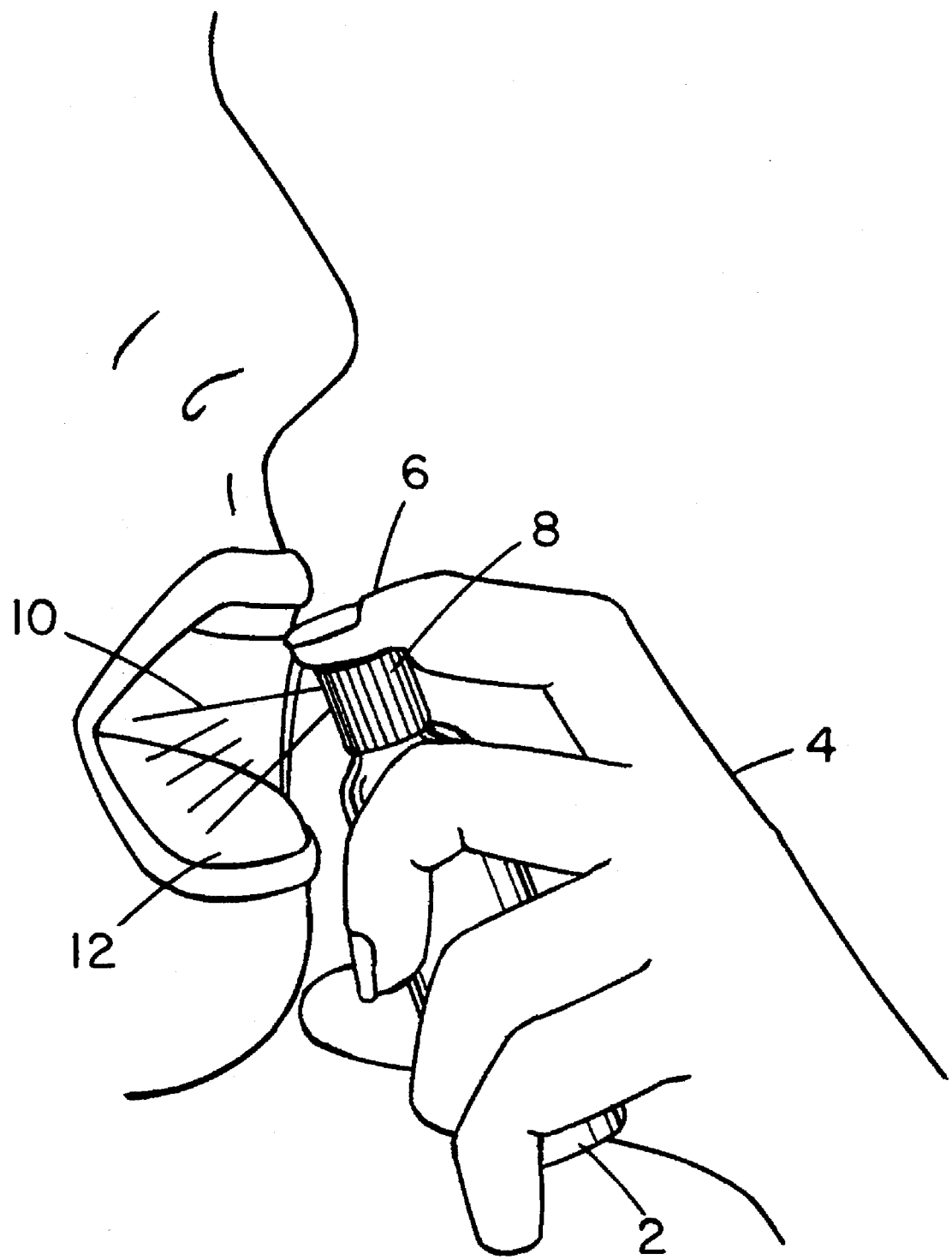

1

METHOD FOR ORAL SPRAY ADMINISTRATION OF CAFFEINE

BACKGROUND OF THE INVENTION

1. Field of the Invention

The invention herein relates to CNS (central nervous system) stimulants. More particularly, it relates to methods of administering CNS stimulant compounds to humans.

2. Description of the Prior Art

Caffeine (1,3,7-trimethylxanthine) is well known as a CNS stimulant; Olin (ed.), Drug Facts and Comparisons, ch. 6, pp. 1116–1118 (1994) and is found in many common beverages; Olin, supra, p. 1116; Caro et al., in American Pharmaceutical Association (APhA), *Handbook of Nonprescription Drugs*, Ch. 16, pp. 364–367 (8th Edn.: 1986). It is also available as an over-the-counter (OTC) oral medication in tablet and capsule form; Olin et al., supra, p. 1118; Caro et al., supra, p. 370.

There have also been several other forms of administration of caffeine described or used. Under a physician's prescription caffeine is available in percutaneous injectable form; Olin et al., supra, p. 1118. Elixirs, gels, drops (with caffeine in suspension) and syrups are mentioned in U.S. Pat. No. 4,778,810. U.S. Pat. No. 5,219,858 describes delivery of serotonin antagonist compositions intended for use in drug withdrawal therapy which contain CNS stimulants, and which may be delivered "via any of the accepted modes of administration for therapeutic agents." Both of the aforesaid patents mention possible transmucosal administration. U.S. Pat. No. 4,963,367 provides an exhaustive list of administrable compounds, including "caffeine-sodium benzoate" in injectable form. No reference mentions or suggests any form of spray administration other than conventional nasal sprays.

Unfortunately however, the known methods of administering caffeine in the form of tablets or capsules are not necessarily acceptable to most people and certainly do not lend themselves readily to convenient use. Most people, for instance, will not carry bottles of tablets, pills, syrups or elixirs with them and be observed taking such products when stimulation is needed. Further, in many instances CNS stimulation is needed when it is simply not possible to take a pill, swallow a spoonful of syrup, etc.; e.g., while driving a car or truck. In addition many people, especially the elderly, cannot swallow pills or tablets. When self-administration methods are inconvenient, few people will bother with administering the material.

Some prior art methods are impractical in other than a medical setting. Percutaneous, parenteral, rectal, transdermal and subcutaneous administration of caffeine are all essentially medical administration procedures, not realistically suitable for self-administration, and certainly not suitable for administration in informal and social settings. Inhalant nasal sprays, although providing some transmucosal administration, are not acceptable for administration of caffeine, since large quantities of the sprayed composition also enter the pulmonary system, and there is a serious risk of interference with proper respiration. Further, use of products such as elixirs, syrups and nasal sprays does not provide for metered administration of caffeine.

Many prior art methods do not provide for stimulation in a rapid manner. In many cases (such as the previously mentioned driving of a vehicle) the user cannot wait for an extended period for the caffeine's stimulatory effect to occur; stimulation is needed promptly. The full caffeine component of a tablet or capsule cannot be transferred through the intestinal walls and assimilated into the central nervous system until the capsule or tablet has completely dissolved in the stomach and intestines. Thus, especially in the most common practical prior art self-administration methods, caffeine only slowly reaches the central nervous system and even then the accumulation of the entire dosage of caffeine in the central nervous system requires a prolonged period of time, which in turn means that the stimulatory effect of the caffeine on the person occurs only slowly.

In view of these problems with the prior art administration methods, caffeine usage is significantly less than it would be if people could easily and discreetly self-administer caffeine when appropriate stimulation is needed and without concern about the social setting, using a method which would provide for rapid stimulatory effect. The present invention provides the ability to accomplish just that.

SUMMARY OF THE INVENTION

The invention herein comprises both a method and an apparatus for easily and conveniently self-administering caffeine combined with a breath freshener. The present invention is based on the discovery that a well known CNS stimulant material, caffeine, can be readily, conveniently and effectively administered to humans by a means neither heretofore recognized nor disclosed by the prior art. I have discovered that by metered oral administration of caffeine, incorporated in a liquid carrier in an atomized spray form and in combination with a breath freshener, directly into a person's mouth in liquid spray or stream form, the caffeine can be absorbed in the human system by swallowing and absorption from the intestinal tract or by absorption through the buccal membranes while the breath freshener provides masking taste to overcome any reluctance that a user might have on the basis of the taste of the caffeine alone. The invention is a unique administration method and device by means of which the stimulatory effect of the caffeine is rapidly realized, and which permits simple and convenient administration of caffeine in a unobtrusive and effective manner, either by self-administration or with the assistance of another person, even in circumstances where the prior art administration methods are inconvenient or impossible to use.

In the broadest form of its method aspect, the invention is a method for administering caffeine to a person which comprises incorporating caffeine in at least a predetermined quantity effective to accomplish CNS stimulation in a human and a breath freshening compound into a physiologically acceptable liquid carrier to form a mixture; placing the mixture into a dispensing device from which the mixture can be ejected as an atomized spray or as a liquid stream: operating the device to eject at least one metered amount of the spray or stream of mixture directly onto the person's tongue; and continuing to convey the spray or steam in metered doses onto the tongue for a period of time sufficient to administer a quantity of caffeine effective to promote CNS stimulation to the person by assimilation into the person's body by oral swallowing or by absorption through buccal membranes. The carrier is preferably purified water; sodium benzoate may also be present to enhance the solubility of the caffeine in the water.

The apparatus of the present invention is for oral spray administration of caffeine to a person in at least a predetermined quantity effective to accomplish CNS stimulation in the person, and comprises a reservoir for containing a liquid mixture of caffeine, a breath freshener and a physiologically acceptable liquid carrier, the caffeine being present in a concentration effective on a daily administration basis to promote CNS stimulation to said person by assimilation into said person's body by oral swallowing or by absorption through buccal membranes after administration onto the person's tongue; pump means for generating a metered quantity of a spray or stream of the liquid, having fluid conduit connection to the reservoir; and control means for manipulating the pump means to eject metered quantities of the mixture as the spray or stream directed onto the person's tongue. The apparatus may generate the spray or stream either mechanically by pump action of the mechanism or through differential pressure, as by having the contents of the reservoir under gas pressure greater than ambient, such that manipulation of the pump mechanism control causes a pressure differential to be created which forces the liquid carrier and caffeine to be withdrawn from the reservoir and ejected as an atomized spray or stream.

BRIEF DESCRIPTION OF THE DRAWING

The single FIGURE of the drawing illustrates a typical spray application utilizing the method and apparatus of the present apparatus.

DETAILED DESCRIPTION AND PREFERRED EMBODIMENT

In order to be effective, caffeine must be administered at times when a person's central nervous system is depressed and CNS stimulation is needed. The most common instances of such depression are indicated by fatigue, drowsiness, and inability to concentrate, and are often caused by boredom, repetitive work, long unbroken periods of highway driving, etc. In the present invention, the unique administration of the caffeine in spray or stream form directly onto the tongue provides for extremely rapid assimilation of the caffeine into the central nervous system and therefore rapid (substantially immediate, in many cases) stimulation of the central nervous system. As noted, this is in marked contrast to the prior art's self-administration procedures, in which caffeine only slowly reaches the central nervous system and even then the accumulation of the entire dosage of caffeine in the central nervous system requires a prolonged period of time, which in turn means that the stimulatory effect of the caffeine on the person occurs only slowly.

The safe and adequate daily quantity of caffeine which can be administered to an adult person is up to 1600 mg/day, with no more than 200 mg per individual dose. Preferably the caffeine will be administered in doses not to exceed an accumulation of 200 mg per four-hour period. Lesser doses should be administered to children and pregnant or lactating women. Excessive doses can cause overstimulation of the central nervous system, resulting in insomnia, dyspnea, headache, restlessness, irritability, mild delirium and tremor. See Olin et al., supra, p. 1118 and Caro et al., supra, p. 364. It is possible to reduce the overall dosage, but the CNS stimulatory effect will be decreased.

The actual spray or stream administration is accomplished by first preparing a liquid mixture comprising a predetermined quantity of caffeine, a breath freshener and a physiologically acceptable liquid carrier. The caffeine and breath freshener are dispersed or dissolved in the carrier. The total concentration of caffeine will depend on the number of dose administrations which are contemplated from the device and the amount of caffeine to be administered each day, considering the volume of the device reservoir. Spray/streams valves are designed to dispense a spray or stream with a metered volume in the range of about 0.10–0.20 ml per individual delivery dose, preferably about 0.15–0.17 ml, and will conveniently have a total capacity of 250–600 individual spray or stream doses, preferably about 350–400 doses. Caffeine concentrations will be such to provide on the order of about 5–100 mg of caffeine delivered onto the tongue per delivery dose. In a typical example, a device is designed to dispense the caffeine mixture as an atomized spray with purified water as the carrier. The device's total spray capacity is 360 individual metered sprays. The mixture has a caffeine concentration sufficient to provide $16\frac{2}{3}$ mg of caffeine per spray, and the recommended useage is three individual spray doses per four-hour period, for a dosage of 50 mg per four-hour period. This may be repeated up to four times per day, for a total daily dosage of 200 mg. It will be understood that many other schedules and individual spray or stream quantities are possible and acceptable.

The carrier may be any suitable liquid which has the appropriate viscosity to permit effective dispensing in spray or stream form, is inert or at least non-toxic to the user, is physiologically acceptable for human consumption, has the capacity to dissolve or disperse suitable concentrations of caffeine, breath freshener, and (where present) sodium benzoate. The preferred carrier is water, although glycerin, ethanol, fruit juices, edible oils and the like may also be used. All carriers will be in purified form from which foreign matter such as bacteria will have been reduced to a quantity not greater than that approved by applicable governmental regulations or, preferably, eliminated substantially totally.

It is known that sodium benzoate increases the solubility of caffeine in water. Consequently it is within the scope of this invention to have sodium benzoate also present in the mixture, so that the concentration of caffeine can be increased in the mixture and greater doses of caffeine can be administered per individual dose. Sodium benzoate is compatible with caffeine and is acceptable for human administration. It does not change the physiological effect of the caffeine, but rather merely permits higher concentrations of caffeine to be present in the mixture in the container and therefore also in each individual dose.

The breath freshener composition which is incorporated into the mixture with the caffeine provides both breath freshener anti-mouth-odor properties (as by reaction or masking) and also serves as a flavorant, to provide a pleasant flavor to the mixture. Unlike in the prior art administration methods described above, where taste was in most cases not a factor, the unique method of administration herein of delivery directly onto the tongue requires that the mixture be palatable, or people will simply not use the method. Since the taste of caffeine, sodium benzoate and/or the carrier may be disagreeable to some users, the breath freshener/flavorant is included to overcome any adverse taste. There are numerous breath freshener materials commercially available which are suitable for administration in liquid form and which are compatible with caffeine and various carriers, and any of these may be used satisfactorily in this invention. The amount of breath freshener which will be administered is not critical, as long as it is sufficient to provide breath freshening and flavorant properties.

The overall viscosity of the mixture will be essentially that of the liquid carrier, which must be sufficiently low that the mixture can be readily atomized and sprayed using conventional pump spraying or gas propelled spraying. The latter uses a gas such as $CO_2$ or a compound which generates a gas, such as nitrogen generation by spontaneous decomposition of azide compounds. The gas propellant must be inert with respect to the liquid carrier, the breath freshener and the caffeine and must be nontoxic and otherwise safe for use by a human.

In order to provide maximum stimulatory effect of the caffeine on the central nervous system on an as-needed basis, while minimizing the risk of over-stimulation, it is recommended that the user self-administer the caffeine in intermittent dosages, allowing the stimulatory effect of each individual dose to act for as long as time as possible, before administering the next quantity. Thus in the present invention it is preferred that the caffeine be administered at at least two separate times during the day, usually spaced apart by the length of time occurring before the symptoms of fatigue, drowsiness, etc. significantly recur. The total cumulative amount of caffeine administered during a four hour period or over the course of a day, regardless of the actual number of administrations, will be no greater than the above-mentioned limits.

The device useful herein is a small device comprised of a housing containing the fluid reservoir and onto which is mounted the operating mechanism, which conveniently fits the hand, and which is easily carried and stored in a pocket, purse, pack, briefcase, or the like. The reservoir for the caffeine/breath freshener/liquid carrier mixture is connected by a fluid conduit to a dispensing head through which the spray or stream is generated. Where the reservoir is under gas the dispensing head may contain essentially only a valve and a nozzle. The valve will be a normally-closed valve which is opened by finger pressure against the closing mechanism (usually a spring) and which is held open long enough for the required amount of mixture to be ejected in spray or stream form into the mouth and onto the tongue. Pressurized devices are not preferred, however, primarily because it is more difficult to control and meter the precise amount of mixture, and thus of caffeine, which is ejected from the device with each operation. The pressurized devices are also somewhat inefficient, in that after a certain period of use, the pressure has often decreased sufficiently to prevent ejecting of the some significant residual quantity of the carrier/caffeine mixture from the device's reservoir, resulting in the waste of caffeine.

More preferred are mechanical pump dispensing devices, as illustrated in the FIGURE, in which the dispensing head is in the form of a small pump mechanism which draws in ambient air and pumps it into the liquid reservoir, where the increase in pressure forces the liquid mixture out through the nozzle in spray or stream form. For instance, in the illustration of the FIGURE the user holds the housing 2 of the device in his or her hand 4 and uses finger 6 to operate dispensing head 8 to cause a metered spray 10 to be sprayed into the user's mouth, and substantially all onto the user's tongue 12. The pump mechanism and the nozzle are designed and calibrated such that each stroke of the pump causes metered emission of a predetermined known quantity of liquid mixture and thus of caffeine. This permits the manufacturer to stipulate the specific number of doses to be used to administer the desired daily cumulative quantity of caffeine. The number of daily doses from a given device will of course be dependent upon the volumetric capacity of the dispensing head; the manufacturer may determine beforehand whether the device is to be equipped with a high volume dispensing spray head and used for a few doses per day of individually large volumes, or to be equipped with a small volume dispensing head, and thus requiring a larger number of lesser volumes per day to obtain a large cumulative dosage. For the most part, the manufacturers will normally prefer the high volume heads with fewer number of doses during the day, since that is most convenient for the user.

The caffeine in the liquid carrier, upon being sprayed in the mouth and onto the tongue, will in part be swallowed and in part be absorbed through the buccal membranes inside the mouth. The swallowed portion is absorbed into the body through the gastrointestinal tract membranes. In both cases the rapidity of the stimulatory effect is markedly greater than that of the prior art, since the user need not wait, for example, for a tablet or capsule to dissolve and slowly release portions of its caffeine content.

It will be evident that the novel and unique method of administration herein represents a far more convenient and readily acceptable method of administration than those methods described in the prior art. A person may carry a small dispenser device in a pocket, purse, briefcase, etc., from which it can be easily removed and discreetly used to provide the desired or recommended quantity of caffeine at any convenient time. The appearance given will be similarly to that seen with use of commercial spray breath fresheners. One can thus readily and conveniently use the product at any time of choice, and obtain a substantially immediate stimulatory effect, a result particularly important for many activities, such as driving a vehicle, operating machinery, studying, or any other activity which required prompt and continual concentration.

This convenient and discreet use of the product through this method will lead to far more effective use of caffeine by people, since there will be no incentive not to have the device readily available. The inconvenience and stigma of having to take pills or capsules publicly or to drink elixirs or syrups (and seeking the water or other drink with which to take such pills or capsules or the spoons or glasses to take such elixirs or syrups) or subject oneself to injections, inhalation or transdermal administration are all avoided, so that there is little or no lack of usage of the present method which such inconvenient and embarrassing methods engendered in the prior art products. Neither is there the prolonged wait for the caffeine administered in the prior art manners to take effect.

It will be evident from the above that there are numerous embodiments of this invention which, while not expressly described above, are clearly within the scope and spirit of the invention. The above is therefore to be considered exemplary only and the invention is to be limited solely by the appended claims.

I claim:

1. A method for administering caffeine to a person from a dispensing device which comprises:

incorporating caffeine in at least a predetermined quantity effective to accomplish CNS stimulation in a human and a breath freshening compound into a physiologically acceptable liquid carrier to form a mixture;

placing the mixture into said dispensing device from which said mixture can be ejected as an atomized spray or as a liquid stream;

operating said device to eject at least one metered amount of said spray or stream of mixture comprising at least 5 mg of caffeine directly onto said person's tongue; and continuing to convey said spray or stream in metered doses onto said tongue for a period of time sufficient to administer at least 50 mg of caffeine, thereby promoting CNS stimulation to said person by assimilation into said person's body by absorption through buccal membranes.

2. A method as in claim 1 wherein said caffeine is administered in cumulative daily quantities of not more than 1600 mg.

3. A method as in claim 2 wherein said caffeine is administered in individual doses of no more than 200 mg/dose.

4. A method as in claim 3 wherein said caffeine is administered in a cumulative quantity of not more 200 mg per four hour period.

5. A method as in claim 1 wherein said device comprises a mechanically operated pump which generates and ejects said liquid spray or stream.

6. A method as in claim I wherein said device comprises a gas pressure operated pump which generates and ejects said liquid spray or stream.

7. A method as in claim 1 wherein said breath freshener comprises a composition which also imparts a palatable flavor to said mixture.

8. A method as in claim 1 wherein said mixture further comprises sodium benzoate.

9. A method as in claim 1 wherein said carrier is selected from the group consisting of water, glycerin, ethanol, fruit juices, edible oils and the like.

10. A method as in claim 9 wherein said carrier is purified water.

* * * * *